United States Patent [19]

Bouwhuis

[11] Patent Number: 4,599,751
[45] Date of Patent: Jul. 15, 1986

[54] PROTECTIVE UNDERGARMENT

[75] Inventor: Harry E. Bouwhuis, Bowmanville, Canada

[73] Assignee: Bouwhuis Protective Undergarment Ltd., Bowmanville, Canada

[21] Appl. No.: 652,015

[22] Filed: Sep. 19, 1984

[30] Foreign Application Priority Data

Sep. 21, 1983 [CA] Canada .................................. 437210

[51] Int. Cl.⁴ .............................................. A41B 9/00
[52] U.S. Cl. ................................... 2/400; 128/138 R
[58] Field of Search .................... 128/138, 133; 2/400, 2/406, 321; 24/74, 75, 77, 78, 163

[56] References Cited

U.S. PATENT DOCUMENTS 407,919 7/1889 Blum ....................................... 24/74
2,783,759 3/1957 Hill ....................................... 128/133

Primary Examiner—Doris L. Troutman

[57] ABSTRACT

The undergarment is in the form of pants composed of chain mail and having a belt which may be locked about a wearer's waist. The pants cannot thereafter be removed from the wearer's body in the absence of a key without the use of tools normally not carried by persons intent upon a sexual attack.

4 Claims, 4 Drawing Figures

U.S. Patent   Jul. 15, 1986   4,599,751 ated in FIG. 4.
PROTECTIVE UNDERGARMENT

BACKGROUND OF THE INVENTION

This invention relates to protective clothing and more particularly to protective pants having locking means for preventing their removal unless desired by the wearer of the pants.

Women have resorted to a variety of different methods to protect themselves from sexual assault. Some women carry weapons such as pistols and knives, some carry aerosol dispensers containing chemicals such as tear gas, mace or the like and some women make use of judo or karate to fend off attack. These methods however are usually not effective where the attack comes by surprise or where a woman is not able to keep her nerve when she becomes aware of an impending attack.

SUMMARY OF THE INVENTION

It is an object of this invention to provide protective pants which can be locked to a woman's body and which when so locked cannot be removed without tools which are not normally carried by a man intent upon a sexual attack. The pants will accordingly foil such an attack whether or not the attack comes by surprise or whether or not the woman maintains her composure when she realizes an attack is imminent.

Another object of this invention is to provide protective pants which may be worn in comfort by a woman and may be easily removed by her when she so desires. The pants may make direct contact with the skin or may be worn comfortably outside a conventional undergarment.

These and other objects are accomplished by a protective undergarment for the lower torso of a wearer comprising: pants extending from the waist to the thighs and being relatively tight fitting to the thighs; a belt connected to the pants adjacent to the waist, both said pants and said belt being composed of flexible material resistent to manual tearing and to severance by a knife or like sharp object; means for fastening said belt selectively tightly about the waist, said belt when so maintained serving to prevent removal of said pants from the lower torso, said belt when disposed loosely about the waist allowing removal of said pants from the lower torso; and a lock integral with said fastening means for causing said fastening means to maintain said belt tightly about the waist.

DESCRIPTION OF THE DRAWING

The invention is described in detail with reference to the accompanying drawing in which.

Like reference characters refer to like parts throughout the description of the drawing.

DESCRIPTION OF THE PREFERRED EMBODIMENT

Figure 1:
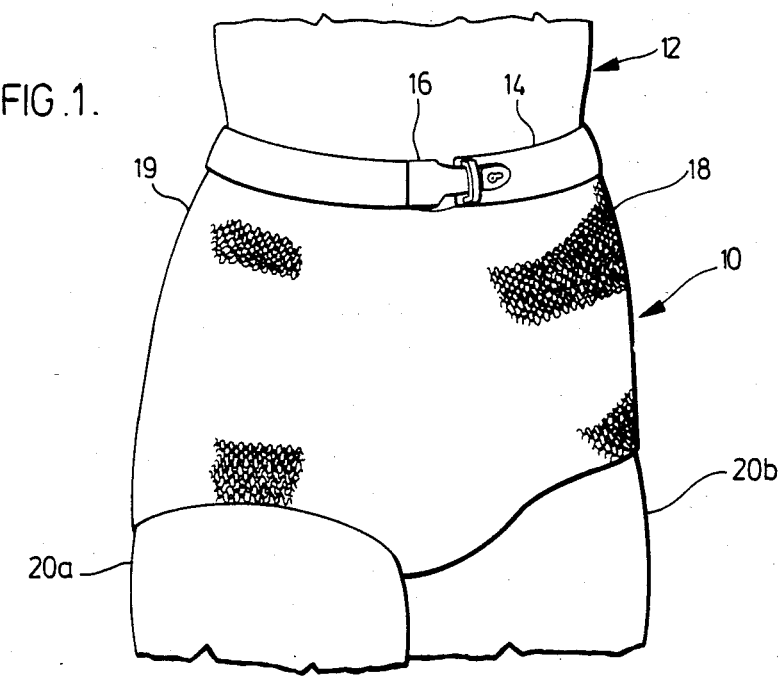
FIG. 1 is a perspective view of the protective garment in conjunction with the lower torso of a wearer.

With reference to FIG. 1 the protective garment of the invention, indicated generally by the numeral 10, is shown in conjunction with the lower torso, generally 12, of a wearer The undergarment comprises a belt 14, means for fastening the belt about the wearer's waist in the form of a buckle 16 and pants 18. The pants extend from the wearer's waist 19 to the thighs 20a,b. As illustrated the pants are relatively tight fitting to the thighs and are held tightly to the waist by means of belt 14.

The pants and belt are composed of flexible material which is resistent to manual tearing and to severance by a knife or a like sharp object. The pants may be composed of chain mail or tough but soft polymeric material. The belt may likewise be composed of tough, soft polymeric material or even chail mail. Whatever material is used, the pants and belt must both be capable of resisting cutting, tearing or any other damage by hand or by knife so that the pants cannot be removed by such method.

Figure 2:
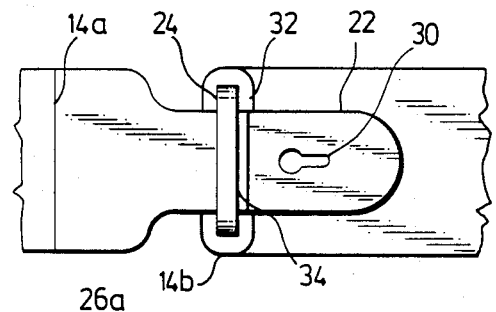
FIG. 2 is an elevation of the buckle for securing the protective undergarment to a wearer.

With reference to FIG. 2 the belt fastening means or buckle therein illustrated is composed of a tongue 22 and a retaining member 24 both of which being fastened to opposite ends 14a,b respectively of the belt. The tongue is provided with a base 25 and a catch 26. The catch is moveable from the position illustrated in FIGS. 3 and 4 in which its upper surface 26a diverges from the plane of base 25 to a position in which its upper surface is flush with the latter plane.

Figure 3:
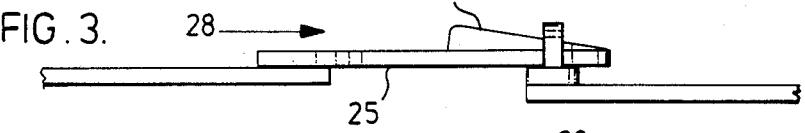
FIG. 3 is a side view of the buckle showing the manner in whick its components are connected to one another.
Figure 4:
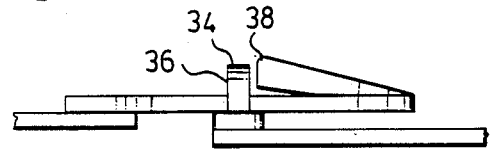
FIG. 4 is a side view of the buckle showing its components in the same position as in FIG. 2.

A spring or other resilient means (not illustrated) is disposed within the catch for maintaining it in the position illustrated in FIGS. 3 and 4 but the catch may be moved to a position flush with base 25 by forcing it manually downward or by moving it in the direction of arrow 28 in FIG. 3 against the retaining member.

A lock (not illustrated) is accommodated within the catch. The lock is of conventional construction and is operated by means of a key which passes through keyhole 30. By means of the lock, the catch can be fixed in the position inclined from the plane of base 25 as illustrated in FIG. 4.

The retaining member is composed of a base 32 and a U-shaped element 34. The base and element define an opening 36 through which the tongue may be passed or inserted.

As illustrated in FIG. 4 the U-shaped element 34 of the retaining member contacts the rear edge 38 of the catch when the tongue has been passed through opening 36. In such position the tongue cannot be removed unless pressure, opposed to the bias of the spring within the catch, is applied to the catch to cause its upper surface to move to a position in which is flush with the plane of base 25. Should the catch be locked in the position illustrated in FIG. 4 of course the catch cannot be moved as indicated.

In operation the protective undergarment of the invention is donned by a woman in the usual manner either directly in contact with her skin or more preferably outside a conventional undergarment. The belt of the protective garment is then tightened about her waist by interconnection of the tongue and retaining member of the buckle. The latter two components are then locked together by means of a key. The undergarment cannot thereafter be removed in the absence of the key without the use of tools normally not carried by persons intent upon a sexual attack.

A woman who wears the undergarment will of course ensure that the key is not readily available when she desires the protection of the pants. She might conceal the key in her purse or to her body or she might keep a key at her place of work and at her home but not about her person.

It will be understood of course that modifications can be made in the preferred embodiment described herein without departing from the scope and purview of the invention as defined in the appended claims.

What I claim as new and desire to protect by Letters Patent of the United States is:

1. A protective undergarment for the lower torso of a wearer comprising: pants extending from the waist to the thighs and being relatively tight fitting to the thighs; a belt connected to the pants adjacent to the waist, both said pants and said belt being composed of flexible material resistent to manual tearing and to severance by a knife or like sharp object; means for fastening said belt selectively tightly about the waist, said belt when so maintained serving to prevent removal of said pants from the lower torso, said belt when disposed loosely about the waist allowing removal of said pants from the lower torso; and a lock integral with said fastening means for causing said fastening means to maintain said belt tightly about the waist.

2. The protective undergarment as claimed in claim 1 wherein said fastening means is composed of a tongue fastened to one end of said belt and a retaining member fastened adjacent to the other end of said belt, said retaining member having an opening into which said tongue may be inserted, said lock being connected to said tongue and preventing removal of said tongue when inserted into said opening.

3. The protective undergarment as claimed in claim 1 wherein said fastening means composed of a tongue fastened to one end of said belt and having a catch biased by resilient means into a locking position; a retaining member having an opening and fastened adjacent to the other end of said belt, said tongue being connected to said retaining member by the application of pressure to said catch opposed to the bias of said resilient means to cause said catch into an unlocking position, then inserting said tongue into said opening and thereafter releasing said pressure whereby said catch maintains said tongue within said opening and prevents removal thereof, said lock being connected to said tongue and operative to maintain said catch in said locking position.

4. The protective undergarment as claimed in claims 1, 2 or 3 wherein said pants are composed of chain mail.

* * * * *